United States Patent
Richards et al.

(10) Patent No.: US 9,449,726 B2
(45) Date of Patent: Sep. 20, 2016

(54) $^{100}$MO COMPOUNDS AS ACCELERATOR TARGETS FOR PRODUCTION OF $^{99m}$TC

(71) Applicant: Washington University, Saint Louis, MO (US)

(72) Inventors: Vernal Richards, Saint Louis, MO (US); Suzanne Lapi, Saint Louis, MO (US)

(73) Assignee: Washington University, Saint Louis, MO (US)

( * ) Notice: Subject to any disclaimer, the term of this patent is extended or adjusted under 35 U.S.C. 154(b) by 30 days.

(21) Appl. No.: 14/293,599

(22) Filed: Jun. 2, 2014

(65) Prior Publication Data
US 2014/0356282 A1  Dec. 4, 2014

Related U.S. Application Data

(60) Provisional application No. 61/829,596, filed on May 31, 2013.

(51) Int. Cl.
*G21G 1/00* (2006.01)
*C01B 31/34* (2006.01)
*A61K 51/04* (2006.01)

(52) U.S. Cl.
CPC ........... *G21G 1/001* (2013.01); *A61K 51/0489* (2013.01); *C01B 31/34* (2013.01); *G21G 2001/0036* (2013.01); *G21G 2001/0042* (2013.01)

(58) Field of Classification Search
CPC ....... A61K 51/00; A61K 51/025; G21G 1/00
See application file for complete search history.

(56) References Cited

U.S. PATENT DOCUMENTS

| 3,833,469 A | 9/1974 | Robson |
| 4,280,053 A | 7/1981 | Evans |
| 4,990,787 A | 2/1991 | Vanderheyden |
| 5,382,388 A | 1/1995 | Ehrhardt et al. |
| 5,802,439 A | 9/1998 | Bennett et al. |
| 7,737,415 B2 | 6/2010 | Casale et al. |
| 8,126,104 B2 | 2/2012 | Schenter |
| 2012/0281799 A1 | 11/2012 | Wells |
| 2013/0301769 A1* | 11/2013 | Schaffer et al. .............. 376/195 |

OTHER PUBLICATIONS

Armas, R.R. Clinical studies with spleen-specific radiolabeled agents. Semin. Nucl. Med. 15(3): 260-275, Jul. 1985.
Ballinger, J.R. 99Mo shortage in nuclear medicine: crisis or challenge? J. Labelled Cmpds. Radiopharma. 53:167-8, Jan. 2010.
Banerjee, S., et al. Evolution of Tc-99m in diagnostic radiopharmaceuticals. Sem. Nuc. Med. 31(4):260-77, Oct. 2001.
Beaver, J.E., Hupf, H. B. Production of 99m Tc on a medical cyclotron: a feasibility study. J. Nuc. Med. 12(11):739-41, 1971.
Biersack, J.P., and Haggmark, L.G. A Monte Carlo computer program for the transport of energetic ions in amorphous targets. Nucl. Instr. Meth. 174:257-69, 1980.
Bigott, H.M., et al. Advances in the production, processing and microPET image quality of technetium-94m. Nucl Med Biol. Oct. 2006;33(7):923-33.
Celler, A. et al. Theoretical modeling of yields for proton-induced reactions on natural and enriched molybdenum targets. Phys. Med. Biol. 56 (2011) 5469-5484.
Chouzier S., et al., Decompositionofmolybdate—hexamethylenetetraminecomplex:Onesingle source routefordifferentcatalyticmaterials J. Solid State Chemistry 184:2668-2677, Aug. 2011.
Dash, A. et al. 99Mo/(99m)Tc separation: an assessment of technology options. Nuclear medicine and biology 2013;40:167-176.
Eckelman, W.C. Unparalleled contribution of technetium-99m to medicine over 5 decades. JACC: Cardio. Imaging. 2(3): 364-8, Mar. 2009.
Von Hippel F.N., et al. Feasibility of Eliminating the Use of Highly Enriched Uranium in the Production of Medical Radioisotopes Sci. Global Security. 14:151-62, 2006.
Gagnon, K., et al., Cyclotron production of (99m)Tc: experimental measurement of the (100)Mo(p,x)(99)Mo, (99m)Tc and (99g)Tc excitation functions from 8 to 18 MeV. Nuclear Med. Biol. 38:907-916, 2011.
Gagnon, K., et al. Cyclotron production of 99mTc: recycling of enriched 100Mo metal targets. Appl Radiat Isot. Aug. 2012;70(8):1685-90.
Gibson, J. High-Temperature Oxide and Hydroxide Vapor Species of Technetium Radiochim. Acta 60:121-126, 1993.
Guérin, B. et al. Cyclotron production of 99mTc: an approach to the medical isotope crisis. J Nucl Med. Apr. 2010;51(4):13N-16N.
Khandaker, M., et al., Nuclear Instruments and Methods in Physics Research Section B: Beam Interactions with Materials and Atoms 262:171-181, 2007.
Lagunas-Solar, M.C., et al., "Cyclotron production of NCA 99mTc and 99Mo. An alternative non-reactor supply source of instant 99mTc and 99Mo—99mTc generators." Int. J. Rad. Appl. Instrum. A, 42: 643-657, 1991.

(Continued)

*Primary Examiner* — Michael G Hartley
*Assistant Examiner* — Jagadishwar Samala
(74) *Attorney, Agent, or Firm* — Saul L. Zackson; Zackson Law, LLC

(57) ABSTRACT

Methods of synthesizing $^{100}$Mo$_2$C and $^{99m}$TcO$_4^-$ are disclosed. Methods of $^{100}$Mo$_2$C generation involve thermally carburizing $^{100}$MoO$_3$. Methods of $^{99m}$TcO$_4$ generation involve proton bombardment of $^{100}$Mo$_2$C in a cyclotron. Yields of $^{99m}$TcO$_4$ can be increased by sintering $^{100}$Mo$_2$C prior to bombardment. The methods also include recycling of $^{100}$Mo$_2$C to form $^{100}$MoO$_3$. SPECT images obtained using $^{99m}$TcO$_4$ generated by the disclosed methods are also presented.

13 Claims, 6 Drawing Sheets

(56) References Cited

OTHER PUBLICATIONS

Lagunas-Solar, M.C., IAEA-TECDOC-1065 "Accelerator production of 99mTc with proton beams and enriched 100Mo targets" in Production technologies for molybdenum-99 and technetium-99m International Atomic, Vienna, Austria: International Atomic Energy Agency 87, 1999.

Lyra, M. et al. Alternative production methods to face global molybdenum-99 supply shortage. Hell. J. Nucl. Med. 14(1):49-55, Mar. 2011.

Nartowski, A.M., et al. Solid state metathesis: synthesis of metal carbides from metal oxides, J. Materials Chemistry 11:3116-3119, 2001.

Nuclear Energy Agency. The Supply of Medical Isotopes; Review of Potential Molybdenum-99/Technetium-99m Production Techniques. Nov. 2010.

Pillai M.R.A. et al. Sustained availability of 99mTc: possible paths forward. J. Nucl. Med. 54:313-23, 2013.

Rösch, F, et al., Thermochromatographic Separation of 94mTc from Enriched Molybdenum Targets and its Large Scale Production for Nuclear Medical Application Radiochim. Acta 64:113-20, 1994.

Rusek, V., et al. Thermal separation of 99mTc from molybdenum trioxide. I. Separation of 99mTc from molybdenum trioxide at tmeratures below 650C Radiochem. Radioanal. Letters 1974;20:15-22.

Scholten, B., et al., Excitation functions for the cyclotron production of 99mTc and 99Mo. Applied Radiation and Isotopes. 51:69-80, 1999.

Takács, S, et al. Evaluation of proton induced reactions on 100Mo: New cross sections for production of 99mTc and 99Mo. J. Radioanalytical and Nuc. Chem. 257(1):195-201, 2003.

Vlcek, J., et al., Thermal separation of 99mTc from molybdenum trioxide. II. Separation of 99mTc from molybdenum trioxide at temperatures above 650C. Radiochem. Radioanal. Letters 20:23-31, 1974.

Wang, H.M., et al. Synthesis of Bulk and Supported Molybdenum Carbide by a Single-Step Thermal Carburization Method. Chem. Materials 19(7):1801-1807, 2007.

Williams W.S., High-temperature thermal conductivity of transition metal carbides and nitrides. J. Amer. Ceramic Soc. 49:156-9, Mar. 1966.

Richards, V. New Orleans Oral Powerpoint Presentation. 245th ACS National Meeting & Exposition, New Orleans, LA presented on Apr. 7, 2013. "Cyclotron produced Tc-99m from Mo (II) compounds. a viable alternative to generator produced Tc-99m.".

Richards, V. Abstract for 245th ACS National Meeting & Exposition presentation. "Cyclotron produced Tc-99m from Mo (II) compounds: A viable alternative to generator produced Tc-99m" Sunday, Apr. 7, 2013.

Ziegler, J.F., et al. SRIM: The Stopping Range of Ions in Matter. Morrisville, NC, USA: LuLu Press, 2008. Chapters 2-3.

Ziegler, J.F., et al. SRIM—The stopping and range of ions in matter (2010). Nuclear Instruments and Methods in Physics Research B 268 (2010) 1818-1823.

\* cited by examiner

$^{100}$MO COMPOUNDS AS ACCELERATOR TARGETS FOR PRODUCTION OF $^{99m}$TC

CROSS-REFERENCE TO RELATED APPLICATION

This application claims the benefit of priority to U.S. Provisional Patent Application 61/829,596 filed May 31, 2013, which is hereby incorporated by reference in its entirety.

STATEMENT REGARDING FEDERALLY SPONSORED RESEARCH OR DEVELOPMENT

The invention was made with government support under DESC0006435 awarded by the U.S. Department of Energy, Office of Science. The government has certain rights in the invention.

INTRODUCTION

The present teachings are in the field of production of radionuclide $^{99m}$Tc.

$^{99m}$Tc, a γ-emitting isotope with a γ-energy of 140 keV and a half-life of six hours, is used worldwide in over 80% of nuclear medicine imaging procedures (Banerjee, S., et al. Sem. Nuc. Med. 31:260-77, 2001; Eckelman, W. C. JACC: Cardio. Imaging. 2: 364-8, 2009; Lyra, M., et al. Hell. J. Nucl. Med. 14:49-55, 2011; Pillai, M. R., et al. J. Nucl. Med. 54:313-23, 2013). Currently, over 600,000 $^{99m}$Tc radiopharmaceutical doses are administered worldwide on a weekly basis (Ballinger, J. R. J. Lavelled Cmpds. Radiopharma. 53:167-8, 2010). The majority of the $^{99m}$Tc used for medical imaging is produced from the decay of $^{99}$Mo, a fission product of $^{235}$U (Pillai, M. R., et al. J. Nucl. Med. 54:313-23, 2013; Ballinger, J. R., J. Labelled Cmpds. Radiopharma. 53:167-8, 2010; Frank, N., et al. Sci. Global Security. 14:151-62, 2006). Nuclear fission of $^{235}$U occurs in nuclear reactors after highly enriched uranium (HEU) undergoes neutron bombardment. $^{99}$Mo is sent to generator manufacturers and the product is supplied to hospital and research facilities as $^{99}$Mo/$^{99m}$Tc generators.

An alternative route is the direct production of $^{99m}$Tc using accelerators (Scholten, B., et al., Applied Radiation and Isotopes. 51:69-80, 1999; Takács, S. et al. J. Radioanalytical and Nuc. Chem. 257:195-201, 2003). This is based on the work of Beaver and Hupf, who used the $^{100}$Mo(p,2n) $^{99m}$Tc reaction route (Beaver, J. and Hupf; H. J. Nuc. Med. 12:739-41, 1971).

$^{100}$Mo is present at 9.6% natural abundance. Guerin et al. (Guerin, B., et al. J. Nuc. Med. 51:13N-6N, 2010), and Gagnon et al. (Gagnon, K., et al., Applied Radiation an isotopes 70:1685-1690, 2012), have both used pressed $^{100}$Mo powder as the target material in the cyclotron bombardment. Guerin's method prepared $^{100}$Mo targets by melting sintered targets on tantalum backings. Gagnon's method uses pressed $^{100}$Mo powder. Both methods use wet separation techniques to extract $^{99m}$Tc from $^{100}$Mo. Guerin et al.'s method utilizes ion-exchange chromatography, while Gagnon et al.'s method employs aqueous bi-phasic extraction chromatography, ABEC™. Gagnon et al.'s method includes a recovery and recycle strategy involving a three step, high temperature hydrogen reduction of the molybdate to $^{100}$Mo. The wet chemical processing techniques of Guerin and Gagnon are multi-chemical, multi-step and can be multi-column operations to a purified pertechnetate. Similarly, the recovery of the target material can entail a multi-step high temperature hydrogen reduction (Gagnon, K., et al., Applied Radiation and Isotopes 70:1685-1690, 2012).

Properties of Mo$_2$C include its high melting point of 2800° C. The chemical stability of Mo$_2$C permits handling at ambient conditions. The high thermal conductivity can also aid with heat dissipation during bombardment. Unlike insulators where thermal conductivity decreases with temperature, Mo$_2$C as an interstitial carbide experiences an increase in thermal conductivity (Williams, W. S. J. Amer. Ceramic Soc. 49:156-9, 1966). Unlike MoO$_3$ where only 25% of the nuclei are Mo, Mo$_2$C has a much higher percentage of Mo nuclei, 66.66%.

Many hospitals and research facilities have installed cyclotrons for $^{18}$FDG production that operate in the energy window where $^{99m}$Tc is produced in relatively high yield, making the cyclotron production of this isotope a viable alternative to the generator produced $^{99m}$Tc.

Previous studies used cyclotron bombardment of $^{94}$MoO$_3$ to produce $^{94m}$Tc, a radionuclide that is used for positron emission tomography (PET), via the $^{94}$Mo (p,n) $^{94m}$Tc reaction, and a thermo-chromatographic method to separate the $^{94m}$Tc from the $^{94}$Mo target material (Bigott, H. M., et al., Nuc. Med. and Biol. 33:923-33, 2006).

Some of the results disclosed herein were presented orally at the 245$^{th}$ ACS National Meeting & Exposition, New Orleans, La. on Apr. 7, 2013 under the title "Cyclotron produced Tc-99m from Mo (II) compounds, a viable alternative to generator produced Tc-99m." An abstract published under the same title did not disclose the use of $^{100}$Mo$_2$C as a target for 99mTc production.

In part because of increasing world demand for $^{99m}$Tc, new methods of producing $^{99m}$Tc are needed.

SUMMARY

The inventors of the present teachings have developed methods of producing $^{99m}$Tc via the $^{100}$Mo(p,2n) $^{99m}$Tc reaction, using a $^{100}$Mo target material of $^{100}$Mo$_2$C.

In some embodiments, $^{100}$Mo$_2$C can be synthesized or generated from $^{100}$MoO$_3$. In various configurations, the synthesis of $^{100}$Mo$_2$C can involve thermally carburizing $^{100}$MoO$_3$.

In various embodiments, the present teachings include methods of synthesizing $^{99m}$Tc, which can include, for example, pertechnetate ($^{99m}$TcO$_4^-$). In various configurations, these methods can comprise or consist of providing, a cyclotron comprising $^{100}$Mo$_2$C, and bombarding the $^{100}$Mo$_2$C in the cyclotron, thereby yielding $^{99m}$Tc such as $^{-99m}$TcO$_4^-$.

In some embodiments, methods of the present teachings include processing of $^{100}$Mo$_2$C by a thermo-chromatographic technique to recycle $^{100}$Mo$_2$C back to $^{100}$MoO$_3$. In various configurations, recycling methods of the present teachings can comprise oxidation at temperatures above 500° C. separation of the $^{99m}$Tc, and collection of $^{100}$MoO$_3$.

In various embodiments, methods of the present teaching include methods of synthesizing pertechnetate ($^{99m}$TcO$_4^-$) that further comprise purifying $^{99m}$Tc$_4^-$ by thermo-chromatography (thermal distillation).

In various configurations, the thermal carburization can comprise (i) converting $^{100}$MoO$_3$ to ammonium heptamolybdate tetrahydrate ((NH$_4$)$_6$Mo$_7$O$_{24}$.4H$_2$O) with NH$_3$(aq) such as about 28% NH$_3$(aq) or 28% NH$_3$(aq), (ii) converting (NH$_4$)$_6$Mo$_7$O$_{24}$.4H$_2$O to a hexamethyltetramine (HMT)-molybdate complex ((NH$_4$)$_4$(HMT)$_2$Mo$_7$O$_{24}$.4H$_2$O) by reacting the (NH$_4$)$_6$Mo$_7$O$_{24}$.4H$_2$O with NH$_3$(aq) and HMT and (iii) heating the dried HMT-molybdate complex in argon atmosphere to yield $^{100}$Mo$_2$C.

In various embodiments, methods of Synthesizing $^{99m}$Tc pertechnetate can include placing a sample comprising $^{100}$Mo$_2$C in a cyclotron, and subjecting the sample to proton bombardment. Following cyclotron bombardment, $^{99m}$Tc pertechnetate can be collected using NaOH, and can be purified using, thermo-chromatography. In various configurations, the thermo-chromatography can comprise or consist of (i) conditioning the column with acidified water such as acidified Millipore™ water, (ii) passing NaOH containing $^{99m}$TcO$_4$$^-$ through an ion-exchange column and (iii) eluting the column with a saline solution. In some aspects, the acidified water can have a pH of about 2.0, or a pH of 2.

In some embodiments, the present teachings include methods of recycling $^{100}$Mo$_2$C to form $^{100}$MoO$_3$. In various aspects, these methods can include (i) washing the $^{100}$Mo$_2$C with 28% NH$_3$(aq), and (ii) using the solution from (i) for synthesis of (NH$_4$)$_6$Mo$_7$O$_{24}$.4H$_2$O.

In various embodiments, the present teachings include methods of imaging. In various configurations, these methods include administering to a subject $^{99m}$Tc produced by the methods disclosed herein, and subjecting the subject to gamma emission detection imaging. In various configurations, the gamma emission detection imaging can comprise or consist of any mode of gamma ray detection known to skilled artisans, such as but not limited to single photon emission computed tomography (SPECT) scanning.

In some embodiments methods of the present teaching can include forming a complex comprising the $^{99m}$Tc and a complexing agent. In various configurations, $^{99m}$Tc produced by the methods disclosed herein can be comprised by a complexing agent, such as, without limitation, methylene diphosphonate (such as MDB-BRACCO™, Bracco Diagnostics Inc., Princeton, N.J.).

Non-limiting examples of imaging that can make use of $^{99m}$Tc produced by methods disclosed herein include a hone scan, myocardial perusion imaging, cardiac ventriculography, functional brain imaging, sentinel node identification, immunoscintigraphy, blood pool labeling, imaging of calcium deposits in heart muscle, and spleen imaging (using a sulfur colloid of $^{99m}$Tc, e.g., as described by Armas, R. R., Semin. Nucl. Med. 15: 260-275, 1985).

In some embodiments, the present teachings include a platinum target holder. In some configurations, a holder can be configured to hold a pressed powder of $^{100}$Mo$_2$C in a cyclotron.

In some embodiments, the present teachings include methods of sintering a pressed powder of $^{100}$Mo$_2$C. In various configurations, the sintering can comprise or consist of heating a pressed powder of $^{100}$Mo$_2$C under vacuum. In some configurations, the heating can consist of heating, the pressed powder of $^{100}$Mo$_2$C under vacuum at 600° C., or about 600° C. In various configurations, such techniques can yield activity greater than 46 mCi, up to 56 mCi, or about 56 mCi following bombardment.

In some embodiments, the present teachings include $^{99m}$TcO$_4$$^-$ having activity greater than 46 mCi, up to about 56 mCi.

The present teachings include, without limitation, the following aspects.

1. A method of synthesizing Mo$_2$C, comprising thermally carburizing MoO$_3$.
2. A method of synthesizing Mo$_2$C, comprising thermally carburizing $^{100}$MoO$_3$.
3. A method of synthesizing Mo$_2$C in accordance with aspect 1, wherein the Mo is $^{100}$Mo.
4. A method of synthesizing pertechnetate ($^{99m}$Tc$_4$$^-$) the method comprising:
   providing a cyclotron comprising $^{100}$Mo$_2$C; and
   bombarding the $^{100}$Mo$_2$C in the cyclotron to yield $^{99m}$TcO$_4$$^-$.
5. A method of synthesizing pertechnetate ($^{99m}$TcO$_4$$^-$) in accordance with aspect 4, further comprising purifying the $^{99m}$TcO$_4$$^-$ by thermo-chromatography.
6. A method of synthesizing $^{99m}$Tc pertechnetate in accordance with aspect 2, wherein the thermally carburizing comprises:
   (i) Converting $^{100}$MoO$_3$ to ammonium heptamolybdate tetrahydrate ((NH$_4$)$_6$Mo$_7$O$_{24}$.4H$_2$O) with 28% NH$_3$(aq), (ii) converting (NH$_4$)$_6$Mo$_7$O$_{24}$.4H$_2$O to a hexamethyltetramine (HMT)-molybdate complex ((NH$_4$)$_4$(HMT)$_2$Mo$_7$O$_{24}$.4H$_2$O) by reacting the (NH$_4$)$_6$Mo$_7$O$_{24}$.4H$_2$O with NH$_3$(aq) and HMT and (iii) heating the dried HMT-molybdate complex in argon atmosphere to give $^{100}$Mo$_2$C.
7. A method of synthesizing $^{99m}$Tc pertechnetate in accordance with aspect 4, wherein the bombarding the $^{100}$Mo$_2$C comprises:
   (i) placing the $^{100}$Mo$_2$C in a cyclotron and (ii) subjecting the sample to proton bombardment.
8. A method of synthesizing $^{99m}$Tc pertechnetate in accordance with aspect 7, wherein the subjecting the sample to proton bombardment comprises subjecting the sample to proton bombardment at a current of from greater than 5 µA up to about 20 µA.
9. A method of synthesizing $^{99m}$Tc pertechnetate in accordance with aspect 7, wherein the subjecting the sample to proton bombardment comprises subjecting the sample to proton bombardment for about 45 minutes, from 45 minutes to 2 hours, or for about 2 hours.
10. A method of synthesizing $^{99m}$Tc pertechnetate in accordance with aspect 4, wherein the $^{99m}$TcO$_4$$^-$ is collected in NaOH.
11. A method of synthesizing $^{99m}$Tc pertechnetate in accordance with aspect 5, wherein the thermo-chromatography comprises:
    (i) conditioning the column with acidified water, (ii) passing NaOH containing $^{99m}$TcO$_4$$^-$ through an ion-exchange column and (iii) eluting the column with a saline solution.
12. A method of synthesizing $^{99m}$Tc pertechnetate in accordance with aspect 5, wherein the acidified water has a pH of about 2.
13. A method of synthesizing $^{99m}$Tc pertechnetate in accordance with aspect 5, wherein the thermo-chromatography comprises:
    (i) conditioning the column with acidified Millipore™ water (pH 2), (ii) passing NaOH containing $^{99m}$TcO$_4$$^-$ through an ion-exchange column and (iii) eluting the column with a saline solution.
14. A method of synthesizing $^{99m}$Tc pertechnetate in accordance with aspect 4, further comprising recycling the $^{100}$Mo$_2$C to form $^{100}$MoO$_3$.
15. A method of synthesizing $^{99m}$Tc pertechnetate in accordance with aspect 14, wherein the recycling comprises:
    (i) washing the with 28% NH$_3$(aq); and
    (ii) using the solution from (i) for synthesis of (NH$_4$)$_6$Mo$_7$O$_{24}$.4H$_2$O.
16. A method of medical imaging, comprising:
    administering to a subject $^{99m}$Tc synthesized by the method of any one of aspects 4-15; and
    subjecting the subject to gamma detection imaging.

17. A method in accordance with aspect 16, wherein the gamma detection imaging comprises or consists of single photon emission computed tomography (SPECT) scanning.
18. A method of medical imaging in accordance with aspect 16, wherein the $^{99m}$Tc is comprised by a complexing agent.
19. A method of medical imaging in accordance with aspect 16, further comprising forming a complex comprising the $^{99m}$Tc and a complexing agent.
20. A method in accordance with aspect 18, wherein the complexing agent is methylene diphosphonate (MDB-BRACCO™, Bracco Diagnostics Inc., Princeton, N.J.).
21. A method in accordance with aspect 16, wherein the imaging is selected from the group consisting of a bone scan, myocardial perusion imaging, cardiac ventriculography, functional brain imaging, sentinel node identification, immunoscintigraphy, blood pool labeling, imaging of calcium deposits in heart muscle, and spleen imaging.
22. A Method of synthesizing pertechnetate ($^{99m}$TcO$_4^-$) in accordance with aspect 4, further comprising:
    prior to the bombarding, pressing the $^{100}$Mo$_2$C to form a compact powder; and
    sintering the compact powder.
23. A method of synthesizing pertechnetate ($^{99m}$TcO$_4^-$) in accordance with aspect 20, wherein the sintering the compact powder comprises heating the compact powder under vacuum at about 600° C.
24. A method of synthesizing $^{99}$mTc pertechnetate in accordance with aspect 4, wherein the bombarding the $^{100}$Mo$_2$C comprises bombarding the $^{100}$Mo$_2$C at a current of from about 1 μA, 1 μA up to 20 μA, or about 20 μA.
24. A method of synthesizing $^{99}$mTc pertechnetate in accordance with aspect 4, wherein the bombarding the $^{100}$Mo$_2$C comprises bombarding the $^{100}$Mo$_2$C at a current of from about 5 μA, 5 μA up to 20 μA, or about 20 μA.
25. A method of synthesizing $^{99}$mTc pertechnetate in accordance with aspect 4, wherein the bombarding the $^{100}$Mo$_2$C comprises bombarding the $^{100}$Mo$_2$C for about 45 minutes, from 45 minutes to 2 hours, or for about 2 hours.
26. A method of synthesizing $^{99}$mTc pertechnetate in accordance with aspect 4, wherein the bombarding the $^{100}$Mo$_2$C comprises bombarding the Mo$_2$C for about 2 hours.
27. A method of synthesizing $^{99}$mTc pertechnetate in accordance with aspect 4, wherein the bombarding the $^{100}$Mo$_2$C comprises bombarding the Mo$_2$C at a current of about 20 μA for about 2 hours.

DETAILED DESCRIPTION

Figure 1:
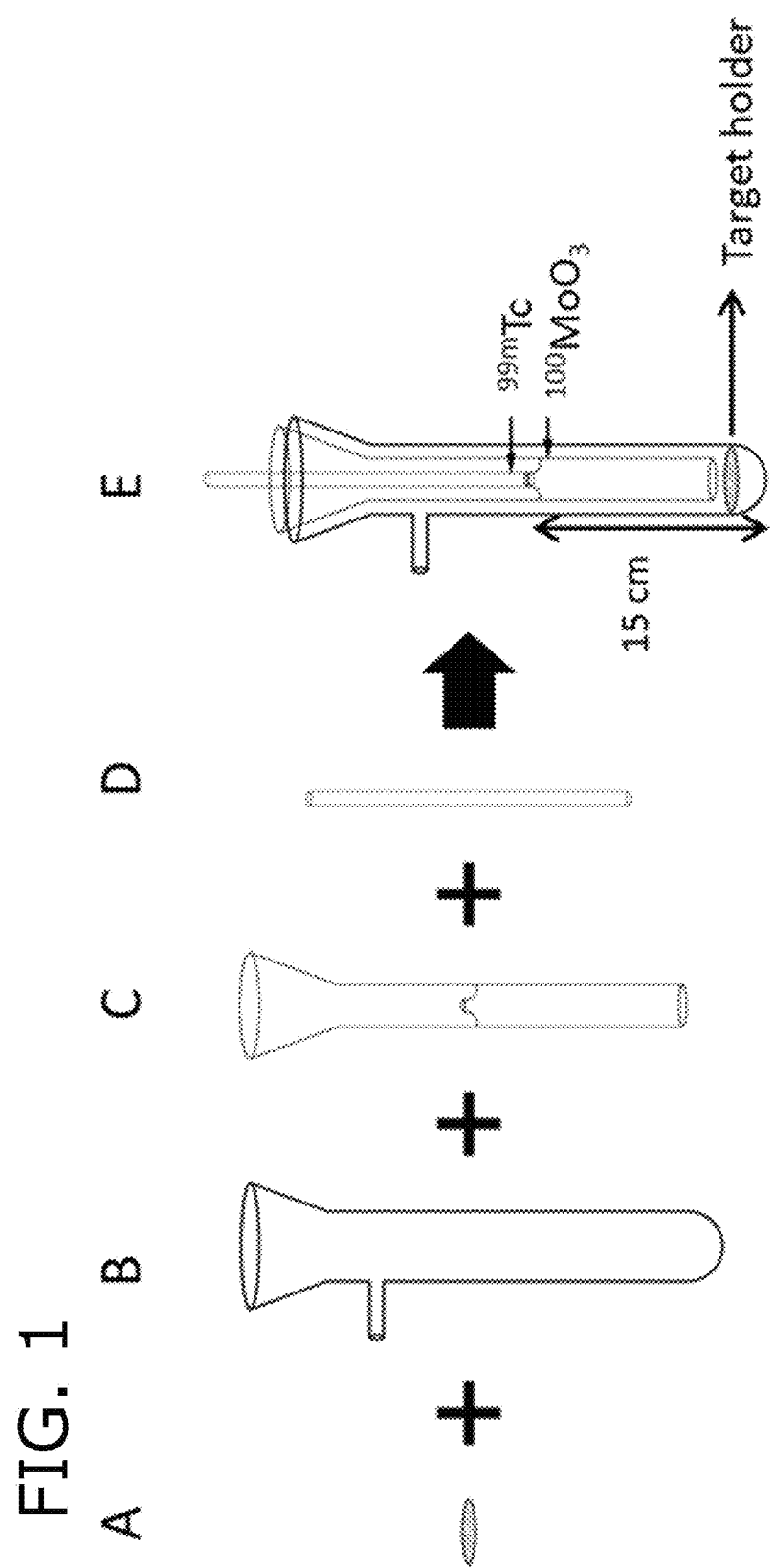
FIG. 1 illustrates an apparatus for target processing.

The present inventors have synthesized $^{100}$Mo$_2$C from $^{100}$MoO$_3$ through a thermal carburization method and have used this as the target for the $^{100}$Mo(p2n)$^{99m}$Tc reaction on a medical cyclotron. This novel target material can be processed using thermo-chromatography to isolate $^{99m}$Tc in high yield. In the process, $^{100}$MoO$_3$ can be recovered in high yield, indicating that using $^{100}$Mo$_2$C as the target material for long term cyclotron can be economically feasible. In various embodiments, the cyclotron produced $^{99m}$Tc can be radio-chemically pure, concentrated in saline solution, and labeled for imaging using prepared kits. NanoSPECT images obtained showed the expected target tissue uptake.

In some configurations, $^{100}$MoO$_3$ can be obtained from a commercial source such as Isoflex USA (San Francisco, Calif.), in high purity such as 99.01% purity. This high isotopic purity of $^{100}$Mo can minimize contamination from other technetium species post bombardment. Methods of synthesis of Mo$_2$C of the present teachings begin with MoO$_3$, which is soluble in an alkaline aqueous environment and can form ammonium heptamolybdate tetrahydrate (HMT) when dissolved in aqueous ammonia. Further reaction of the heptamolybdate with HMT can result in ligand exchange, where two of the ammonium ligands are replaced by HMT. In some configurations, the presence of the ammine in bonding sphere can facilitate the reduction of Mo from the +6 oxidation state to the +2 state while the excess HMT can act as the carbon source while being heated. In some configurations, before being subjected to heat, the HMT-Mo complex can be dried. In various configurations, elemental analysis can reveal the presence of oxide (if present) in the Mo$_2$C while XRD can identify the phase as Tugarinovite MoO$_2$, which matches ICDD® card 01-074-6246 (The International Centre for Diffraction Data®, Philadelphia, Pa.). In other configurations, a reducing gas, such as 4% H$_2$, Ar mixture while subjecting, the material to heat can be used (Chouzier S., et al., J. Solid State Chemistry 184:2668-2677, 2011. Although faced with minute amounts of oxide through the present synthesis convention, methods of the present teachings can use a single source precursor which can eliminate the use and need for temperatures in excess of 1000° C. or the need for alkali earth carbides such as calcium carbide to be used as the carbon source (Nartowski, A. M., et al., J. Materials Chemistry 11:3116-3119, 2001).

In various embodiments, processing and purification can be carried out on the bombarded target material. Thermo-chromatographic separation has proven itself as an efficient method for the separation of Mo and Tc species (Bigott, H. M., et al., Nuc. Med. and Biol. 33:923-33, 2006; Rusek. V., et al., Radiochem. Radioanal. Letters 1974; 20:15-22; Vlcek, J., et al., Radiochem. Radioanal. Letters 20:23-31, 1974; Rösch, F, et al., Radiochim. Acta 64; 113-20, 1994; Dash, A., et al., Nuclear medicine and biology 2013; 40:167-176). Dash et al. list the high radio-nuclidic purity of $^{99m}$Tc attained, and the repeated use of the same set up and the ready recycling of target material as some of the strengths of using this separation method (Dash. A., et al., Nuclear medicine and biology 2013; 40:167-176). Under these conditions, Mo$_2$C undergoes oxidation to MoO$_3$ which then readily sublimes at a lower temperature than Mo$_2$C, thus enhancing the feasibility of this process. It should be noted that under these processing conditions platinum can serve as target holder material due to its inert nature and high melting point.

In various embodiments of the present teachings, Tc can be recovered by rinsing the glassware with 0.1 mM NaOH. Radio-ITLC analysis of the recovered $^{99m}$Tc revealed that a small amount of $^{99m}$TcO$_3$ (5%) (Rösch, F, et al., Radiochim. Acta 64:113-20, 1994; Gibson, J., Radiochim. Acta 60:121-126, 1993) was present along with $^{99m}$TcO$_4^-$. Purification of the wash with Sep-Pak® light alumina N cartridge (Waters Corporation, Milford, Mass.) conditioned by acidified Millipore (ENID Millipore, Billerica, Mass.) water (pH 2) resulted in only the $TcO_4^-$ species. The acidified column holds the pertechnetate ion and allows any neutral technetium species to readily pass through. Eluting this cartridge with 400 μL saline solution was effective with a 71% to 75% activity recovery. In some configurations, gamma spectroscopic analysis can allow for the calculation of the activities produced at the end of bombardment. Unfortunately, although several groups have measured the $^{100}Mo(p,2n)$ $^{99m}Tc$ cross section, significant variability is noted among the values reported (Lagunas-Solar, M. C., IAEA-TEC-DOC-1065, Vienna, Austria: International Atomic. Energy Agency 87, 1999; Scholten, B., et al., Applied Radiation and isotopes 51:69-80, 1999; Takács, S., et al., J. Radioanalytical Nuclear Chem. 257:195-201, 2003; Gagnon, K., et al., Nuclear Med. Biol. 38:907-916, 2011; Khandaker, M., et al., Nuclear Instruments and Methods in Physics Research Section B: Beam Interactions with Materials and Atoms 262: 171-181, 2007). To compare our results to theoretical values, cross section values were chosen for those plots that showed greater agreement between each other. Thus the cross section values for, Sholten (Applied Radiation and Isotopes 51:69-80, 1999), Takas (J. Radioanalytical Nuclear Chem. 257:195-201, 2003) and Khandaker (Nuclear Instruments and Methods in Physics Research Section B: Beam Interactions with Materials and Atoms 262:171-181, 2007) were used in the determination of the theoretical yields. Actual yields for this study were determined to be an average of 84% for the various currents employed, along with their percentage yield, Table 1. These high yields indicate that $Mo_2C$ is an effective target material for the $^{100}Mo(p, 2n)$ $^{99m}Tc$ reaction. In addition to the high yields, the radionuclidic impurities produced in this reaction, $^{95}Tc$ and $^{96}Tc$ were relatively low.

To establish the labeling efficiency of the cyclotron produced $^{99m}Tc$ and its imaging capabilities, animal studies were conducted using CD1 mice. $^{99m}Tc$-MDP was prepared in high yield and purity using commercially available reagents. SPECT images showed accumulation of $^{99m}Tc$ in the bones and joints, with early time point images showing activity in the kidneys and bladder as expected. SPECT images suggest high activity uptake in the cervical, thoracic and lumbar regions of the backbone and major joints. The uptake in the backbone appears relatively uniform.

Methods

The methods described herein utilize laboratory techniques well known to skilled artisans, and guidance can be found in laboratory manuals and textbooks such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999; Hedrickson et al., Organic Chemistry 3rd edition, McGraw Hill, New York, 1970; Carruthers, W., and Coldham, I., Modern Methods of Organic Synthesis (4th Edition), Cambridge University Press, Cambridge, U.K., 2004; Curati, W. L., Imaging in Oncology, Cambridge University Press, Cambridge, U.K., 1995; Welch, M. J., and Redvanly, C. S., eds. Handbook of Radiopharmaceuticals: Radiochemistry and Applications, J. Wiley, New York, 2003. Methods of administration of pharmaceuticals and dosage regimes, can be determined according to standard principles of pharmacology well known to skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. As used in the present description, the singular forms "a", "an" and "the" are intended to include the plural forms as well, unless the context indicates otherwise.

Hexamethyltetramine (HMT) and 28% aqueous ammonia ($NH_3.H_2O$) were purchased from Aldrich USA (St. Louis, Mo.) and used as received. $^{100}MoO_3$ was purchased from Isoflex USA (San Francisco, Calif.) and used was received. MDP-BRACCO™ was purchased from Triad Isotopes, Inc. (Orlando, Fla.) and used as received. Isoflurane was purchased Baxter (Deerfield, Ill.) and used as received.

Synthesis of Ammonium heptamolybdate (Leopold Gmelin R J M. Gmelin's Handbuch für Anorganische Chemie: Verlag Chemie,1935). Enriched $^{100}MoO_3$ was used as the molybdenum source for the synthesis of ammonium molybdate. The full isotopic composition of the material as given by the supplier (Isoflex USA, San Francisco, Calif.) was $^{92}Mo$ (0.09%), $^{94}Mo$ (0.06%), $^{95}Mo$ (0.10%). $^{96}Mo$ (0.11%), $^{97}Mo$ (0.08%), $^{98}Mo$ (0.55%) and $^{100}Mo$ (99.01%), 1.00 g of $^{100}MoO_3$ was dissolved in 10 ml of 28% aqueous ammonia ($NH_3.H_2O$) solution while stirring. The resulting clear solution was evaporated slowly to dryness at 40° C.

Synthesis of Ammonium heptamolybdate—HMT complex and Molybdenum carbide (Wang, H. M., et al. Chem. Materials 19:1801-1807, 2007).

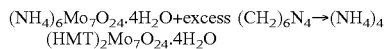

$(NH_4)_6Mo_7O_{24}.4H_2O$+excess $(CH_2)_6N_4 \rightarrow (NH_4)_4(HMT)_2Mo_7O_{24}.4H_2O$ 0.800 g of ammonium molybdate and 0.900 g of hexamethyltetramine (HMT) were dissolved in 20 ml of 28% $NH_3$ solution while stirring. The solution was allowed to evaporate to dryness under air at room temperature after which the resulting solid was subjected to drying under vacuum at 40° C. for 3hours. The solid obtained (1.550 g) was crushed to a fine powder using a mortar and pestle, after which it was loaded in a quartz boat and placed inside a quartz tube of a horizontal furnace. Heating was carried out under argon flow.

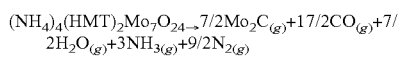

$(NH_4)_4(HMT)_2Mo_7O_{24} \rightarrow 7/2Mo_2C_{(g)}+17/2CO_{(g)}+7/2H_2O_{(g)}+3NH_{3(g)}+9/2N_{2(g)}$ The temperature of the furnace was increased by step by step heating at a rate of 10° C. per minute until a temperature of 700® C. was reached. Heating was maintained at this temperature for 2 hours after which it was increased to 900° C. and heating continued for an additional 2 hours. On cooling the powder was removed, ground with a mortar pestle and stored in air at room temperature for further use.

Target preparation and irradiation. A platinum disc with a diameter of 19 mm, and a thickness 0.16 mm, containing a dimple with diameter of 6.35 mm and height of 1.01 mm. (Electronic Space Products International) was used as the target holder for the cyclotron bombardment of $^{100}Mo_2C$. Approximately 50 mg of $^{100}Mo_2C$ was transferred to the cylindrical dimple located in the center of the platinum disc. The powder was pressed at 5000 psi for 30 seconds to secure it in place, after which the target was mounted into the cyclotron for bombardment. Proton irradiations were carried out using the CS-15 (Cyclotron Corp.) at Washington University. Production runs were conducted in the 15→10 MeV energy window determined by SRIM software (Biersack, J.

P., and Haggmark, L. G. Nucl. Instr. Meth. 174:257-69, 1980; Ziegler, J. F., et al. SRIM: The Stopping Range of Ions in Matter. Morrisville, N.C., USA: LuLu Press, 2008), and at 3, 4 and 5 μA respectively. For each μA, the total μAhr was varied from 1 to 3 in successive runs.

Target Processing. After bombardment, the target was allowed to decay for two hours before being processed in order to allow short lived isotopes ($^{100}$Tc, $^{96m}$Tc) to decay. To extract the $^{99m}$Tc from the irradiated target material, a sublimation method described by Vleck et al. (Vleck, J., et al. Radiochem. Radioanal. Letters. 20:23-31, 1974; Rusek, V., et al., Radiochem. Radioanal. Letters. 20:15-22, 1974) was employed. Custom quartz glassware based on the design put forward by Rösch et al. (Rösch, F., et al. chim. Acta. 64: 113-120, 1994) was used for the separation. The individual pieces and the complete arrangement of the apparatus are shown in FIG. 1. As shown in FIG. 1, the apparatus includes Platinum target holder (FIG. 1A), outer (FIG. 1B), middle (FIG. 1C) and inner (FIG. 1D) quartz tubes, along with the assembled apparatus (FIG. 1E). The assembled glassware with the target in the location was inserted into a preheated furnace at 850° C. Moist air was pumped into the apparatus, via the spout-like opening on tube B. Moist air was obtained by pumping air through a water-Filled bubbling tube. Heating under these conditions continued for 20 minutes and the $^{99m}$Tc and $^{100}$Mo compounds were deposited in tubes D (~250° C.) and C respectively. The deposition is temperature dependent, thus $^{100}$Mo deposits lower down in tube C at a higher temperature zone (~500ϕ C.). Heating under these conditions converts the $^{100}$Mo$_2$C to $^{100}$MoO$_3$. As a safety measure, a small piece of glass wool was placed over the opening of tube D to ensure that small radioactive particulates were not released into the atmosphere. After the process was complete, Tube D containing the $^{99m}$Tc compound was allowed to cool for ~5 minutes, after which it was washed with 8 ml of hot $1.0 \times 10^{-4}$ M NaOH.

Radionuclidic and Radiochemical purity analysis. 10 μL of the resulting solution was diluted to 1000 μL using Millipore water and analyzed on a high purity Ge gamma spectrometer (Canberra) 5 minutes after obtaining the NaOH solution. Using the peak areas and peak efficiencies, radioactivity quantities were subsequently determined and back calculated to end bombardment (EOB). To determine the identities and quantities of long lived radionuclidic impurities, the solution was allowed to decay for a minimum of seventy two hours after which the analysis was repeated where peak data was collected for 6 h.

Radiochemical purity of the $^{99m}$TcO$_4^-$ in NaOH was determined by instant radio-thin layer chromatography (ITLC) using Alumina oxide TLC plates and acetone as the developing solvent. Analysis was performed on a Bioscan System 200 imaging scanner running the WinScan 3 software.

Sep-Pak Light alumina N cartridges (Waters, Milford, Mass.) were used to purify and concentrate the $^{99m}$TcO$_4^-$ for radiochemistry and animal studies. The column was first conditioned with 8 ml of acidified Millipore water (pH 2). The water was acidified with 2 M HCl by drop wise addition until the desired pH was reached. After conditioning, 8 ml of NaOH containing $^{99m}$TcO$_4^-$ was then slowly passed through the column, followed by elution with 400 μL of saline solution resulting in the final purified product. Radiochemical purity of the final product was also determined by radio-ITLC.

In order to examine the efficiency of recovery of $^{99m}$Tc through the sublimation process, a separate target was bombarded under identical conditions as those processed and entirely dissolved in 10 ml of 30% H$_2$O$_2$. 10 μL of this raw target peroxide solution was then subjected to the same dilution and Ge gamma spectrometer analysis as performed above.

Preparation of $^{99m}$Tc-methylene diphosphonate ($^{99m}$Tc-MDP) and Animal Imaging Studies. All animal studies were approved by the Animal Studies Committee at Washington University. $^{99m}$Tc-MDP was prepared using commercially available kits. 3.9 mg of a sterile lyophilized powder containing methylene diphosphonate as the main constituent, under the trade name MDP-BRACCO™ (Bracco Diagnostics Inc., Princeton, N.J.) was dissolved in 135 μL saline solution. From this solution 10 μL was pipetted and added to the 400 μL of $1.6 \times 10^8$ Bq (4.3 mCi)$^{99m}$TcO$_4^-$ containing saline solution. Radio-ITLC was performed on this solution as described above. 100 μL of the prepared radiopharmaceutical with an activity of $2.0 \times 10^7$ Bq (0.55 mCi) was injected into one month old normal CD1 mice via tail vein followed by small animal SPECT/CT imaging (nanoSPECT, Bioscan, Washington D.C.). CT scans were performed using a tube voltage of 45 kV and a scan time of 1.5 seconds per projection while the animals were anesthetized by isofluorane. SPECT data were collected by monitoring in as helical scan at 45 projections and 60 seconds per projection using a 9-pinhole low energy collimator. SPECT images were collected for 45 minutes at 1.5, 3 and 4 hours post injection. The CT and SPECT images were reconstructed and colocalized using InVivoScope (inviCRO, LLC, Boston Mass.) and HiSPECT (Bioscan, Washington, D.C.).

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

This example demonstrates the target synthesis of $^{100}$Mo$_2$C.

Figure 2:
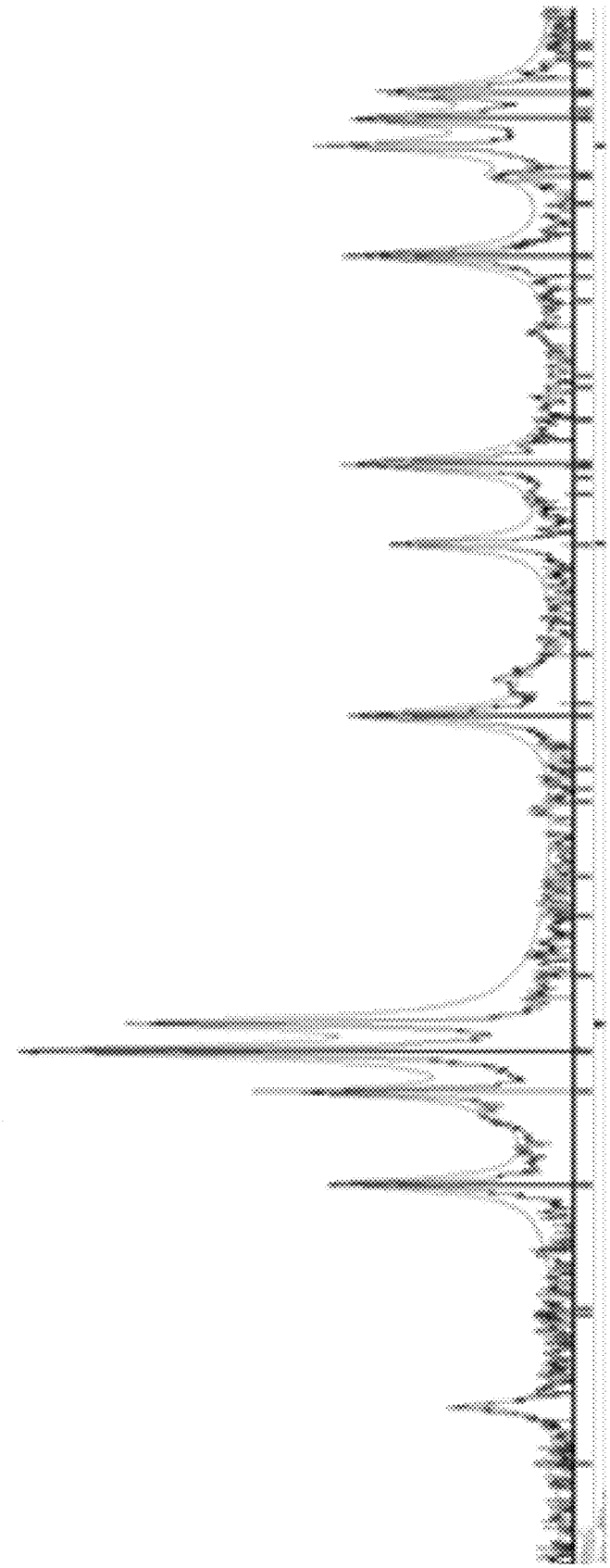
FIG. 2 illustrates x-ray differentiation pattern for $^{100}$Mc$_2$C sample.

Enriched $^{100}$Mo$_2$C was synthesized from enriched $^{100}$MoO$_3$ using a thermal carburization method. Three main steps were involved in the synthesis of the desired Mo$_2$C. The initial step involved the conversion of $^{100}$MoO$_3$ to ammonium heptamolybdate tetrahydrate (($NH_4)_6Mo_7O_{24} \cdot 4H_2O$) with 28% NH$_3$(aq). ($NH_4)_6Mo_7O_{24} \cdot 4H_2O$ yield was consistently averaged at 99%±0.7%. The second step involved the conversion of ($NH_4)_6Mo_7O_{24} \cdot 4H_2O$ to a HMT-molybdate complex (($NH_4)_4(HMT)_2Mo_7O_{24} \cdot 4H_2O$) by its reaction in 28% NH$_3$ (aq) with hexamethyltetramine (HMT). The third step involved heating the dried HMT-molybdate complex in argon atmosphere to give $^{100}$Mo$_2$C with an average yield of 96% for this step. The process was repeated starting with recycled $^{100}$Mo$_2$C (from previous irradiation and sublimation separation) resulting in a yield of 93%. Elemental analysis (Galbraith Laboratories, Knoxville Tenn.) showed the following composition Mo—87%, C—7.2%. Theoretical composition was calculated to yield, Mo—93%, C—6.2%. The X-ray diffraction (XRD) pattern is shown in FIG. 2. The major component is $^{100}Mo_2C$, and matched ICDD card 04-008-1889. In FIG. 2, the overlay of purple spectra indicates $Mo_2C$ reference standard. The results illustrate that this chemistry is amenable to recycling.

Example 2

This example illustrates target preparation, bombardment and processing.

Using Pt as the target holder. $^{100}Mo_2C$ powder targets were pressed at 5000 psi for bombardment. The integrity of the powder was preserved during the bombardment period. While processing, the target by thermal chromatography using moist air, hot $^{100}MoO_3$ (yellowish) was deposited below the constriction in tube C, and $^{99m}Tc$ as pertechnetate ($^{99m}TcO_4^-$) was deposited in tube D. Confirmation of the yield of $^{99m}Tc$ deposited in tube D was Confirmed post thermo-chromatography by using a dose calibrator. The depth to which the thermo-chromatography apparatus was lowered into the vertical furnace was 15 cm as indicated in FIG. 1. Washing tube D with hot (~100° C.) NaOH resulted in near quantitative recovery of $^{99m}Tc$. In various aspects, the total processing time can typically be 45 minutes or less, with about 20 minutes required for the thermal chromatography process. In some embodiments, complete dissolution of targets irradiated under identical conditions using 30% $H_2O_2$ after bombardment was employed and the activities obtained were compared to recovered values obtained via thermo-chromatography, in order to evaluate the recovery efficiency of the chromatography process.

Example 3

This example illustrates the purification of $^{99m}Tc$.

Radio-ITLC analysis performed on recovered $^{99m}Tc$ revealed that a small amount of $^{99m}TcO_3$ (5%) was present along with $^{99m}TcO_4$. Purification of the wash with a Sep-Pak® light alumina N cartridge (Waters Corp., Milford, Mass.) conditioned by acidified Millipore water (pH 2) (EMD Millipore, Billerica, Mass.) resulted in only pertechnetate. Eluting this cartridge with 400 μL saline solution was effective in releasing the pertechnetate with a 71% to 75% activity recovery.

Example 4

This example illustrates an analysis of radionuclidic impurities.

Figure 3:
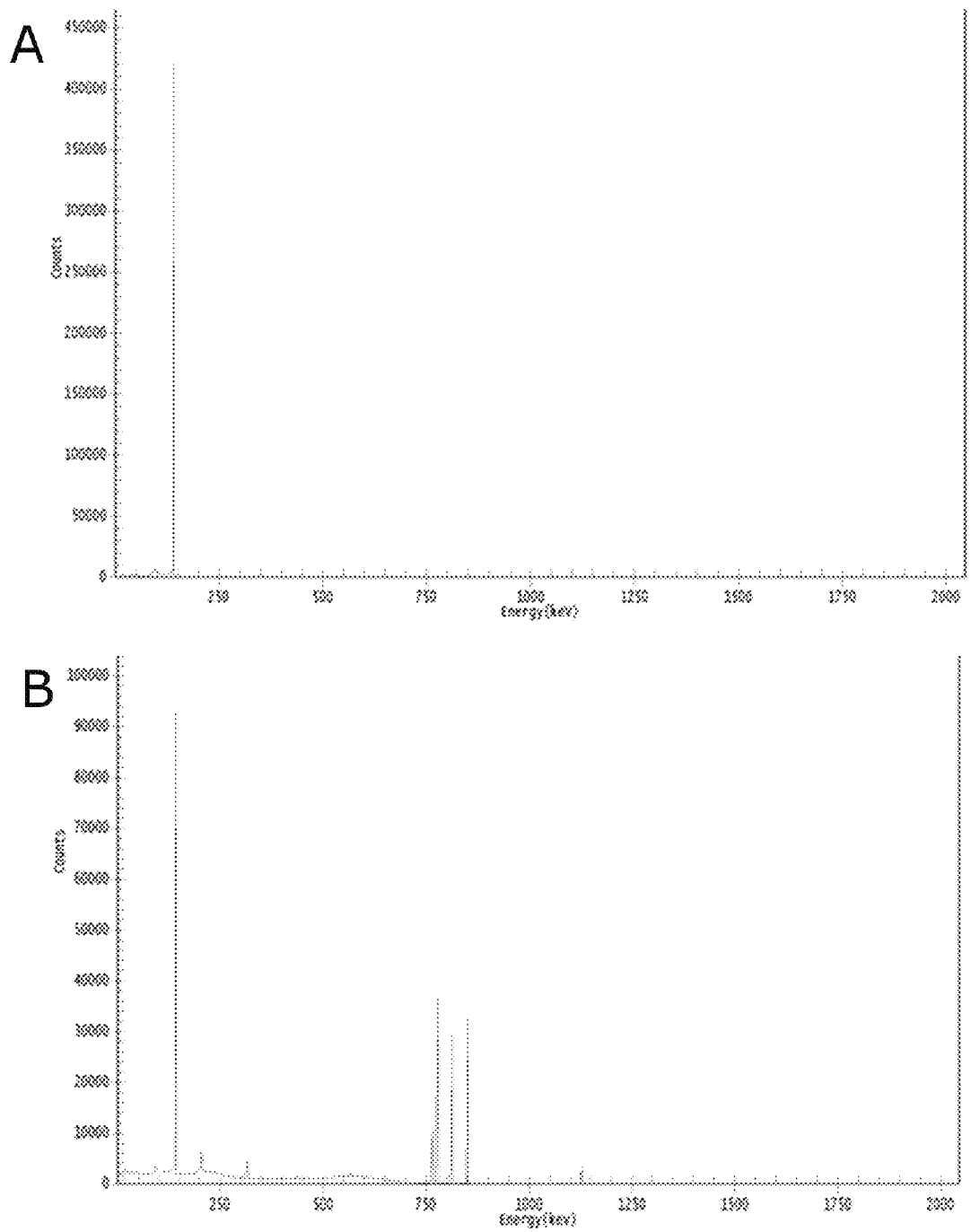
FIG. 3A and FIG. 3B illustrate gamma spectroscopy plots of Tc samples following end of bombardment.

FIG. 3A illustrates a Gamma Spectroscopy plot for $^{99m}Tc$ sample at 4 hours post end of bombardment (EOB). FIG. 3B illustrates a Gamma Spectrometer plot of $^{99m}Tc$, $^{96}Tc$ and $^{95}Tc$ at 85 hours post EOB. Scan time was 6 hours. The gamma-ray spectrum in FIG. 3A shows the characteristic 140 keV peak for $^{99m}Tc$. Table 1 lists the calculated activities corrected to EOB along with the percent recovery for the various parameter settings employed.

TABLE 1

Recovery Radioactivity/Percent Recovery

|  | 3 μA | 4 μA | 5 μA |
|---|---|---|---|
| 1 μAhr | 7.4 × 10$^7$ Bq/66% | 7.4 × 10$^7$ Bq/66% | 7.4 × 10$^7$ Bq/66% |
| 2 μAhr | 1.9 × 10$^8$ Bq/83% | 1.9 × 10$^8$ Bq/83% | 2.1 × 10$^8$ Bq/97% |
| 3 μAhr | 3.1 × 10$^8$ Bq/97% | 3.1 × 10$^8$ Bq/97% | 3.1 × 10$^8$ Bq/97% |

Radionuclidic impurities were identified following a 6 hour scan on samples where $^{99m}Tc$ was allowed to decay for 72 hours post irradiation. A gamma-ray spectrum of an analysis for long-lived impurities is shown in FIG. 3B. In addition to the peak at 140 keV other peaks at various energies became more conspicuous. Based on their energies peaks were assigned to $^{95}Tc$ and $^{96}Tc$. Those associated with $^{95}Tc$ occurred at the following energies, 204 keV and 765 keV, with branching ratios of 63% and 94% respectively. Peaks at 778 keV, 812 keV, 850 keV and 1127 keV were assigned to $^{96}Tc$, with branching ratios of 99%, 82%, 97% and 15% respectively. The percentages of these impurities expressed relative to $^{99m}Tc$ are shown in Table 2.

TABLE 2

Average Isotopic Impurities at EOB.
Values expressed as a percentage relative to $^{99m}TC$.

| $^{99m}TC$ | $^{96}TC$ | $^{95}TC$ |
|---|---|---|
| 100% | 0.03% | 8.6 * 10$^{-6}$% |

Calculated activities for $H_2O_2$ processed targets show good agreement with activities for thermal chromatography processed targets indicating near quantitative recovery.

Example 5

This example illustrates the recycling of $^{100}Mo_2C$ target material to $^{100}MoO_3$.

Figure 4:
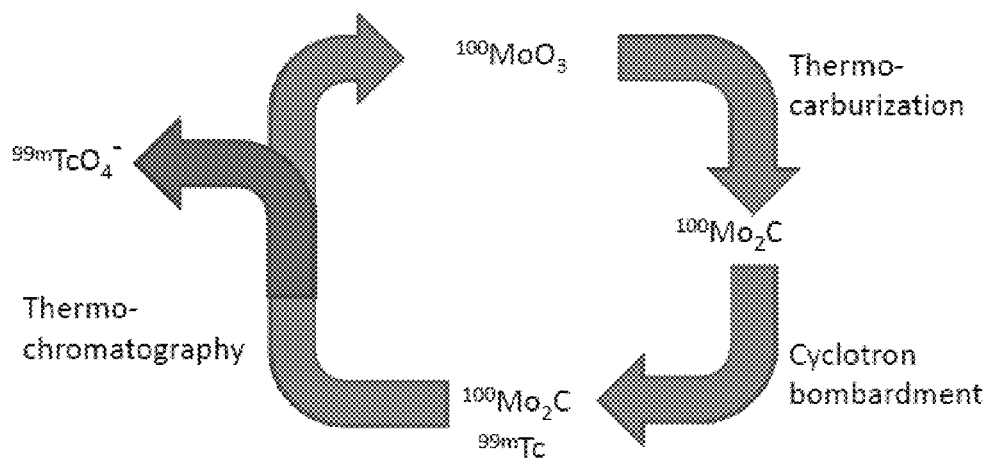
FIG. 4 illustrates life cycle of MoO$_3$ in $^{100}$Mo(p,2n)$^{99m}$Tc production method.

As the thermal chromatography process (thermal distillation) results in a conversion of the $^{100}Mo_2C$ target material to $^{100}MoO_3$, a life cycle recycling process was developed. The life cycle of $MoO_3$ in $^{100}Mo(p,2n)^{99m}Tc$ production method is illustrated in FIG. 4. To maximize the mass of $^{100}MoO_3$ recovered after distillation, tube B was used for at least three trials before any attempt was made to recover this material. Removal was effected by gentle scraping. However scraping was not enough to get all the material so tube B was washed with 28% $NH_3(aq)$ to dissolve the material and this ammonia solution was stored for further use in the synthesis of $(NH_4)_6Mo_7O_{24} \cdot 4H_2O$. The recovered $^{100}MoO_3$ was heterogeneous, containing powdery and spindle-like phases. $^{100}MoO_3$ was converted to $^{100}Mo_2C$ as described above with an average efficiency of 85%. In the synthesis of $(NH_4)_6Mo_7O_{24} \cdot 4H_2O$ using recovered the spindle-like crystals were not readily soluble in the ammonia solution so heating to 50° C. became necessary for complete dissolution. On using $^{100}Mo_2C$ obtained from recycled $^{100}MoO_3$, activities were identical to those obtained using fresh $^{100}MoO_3$.

Example 6

This example illustrates preparation of $^{99m}Tc$-MDP and imaging in small animals.

Figure 5:
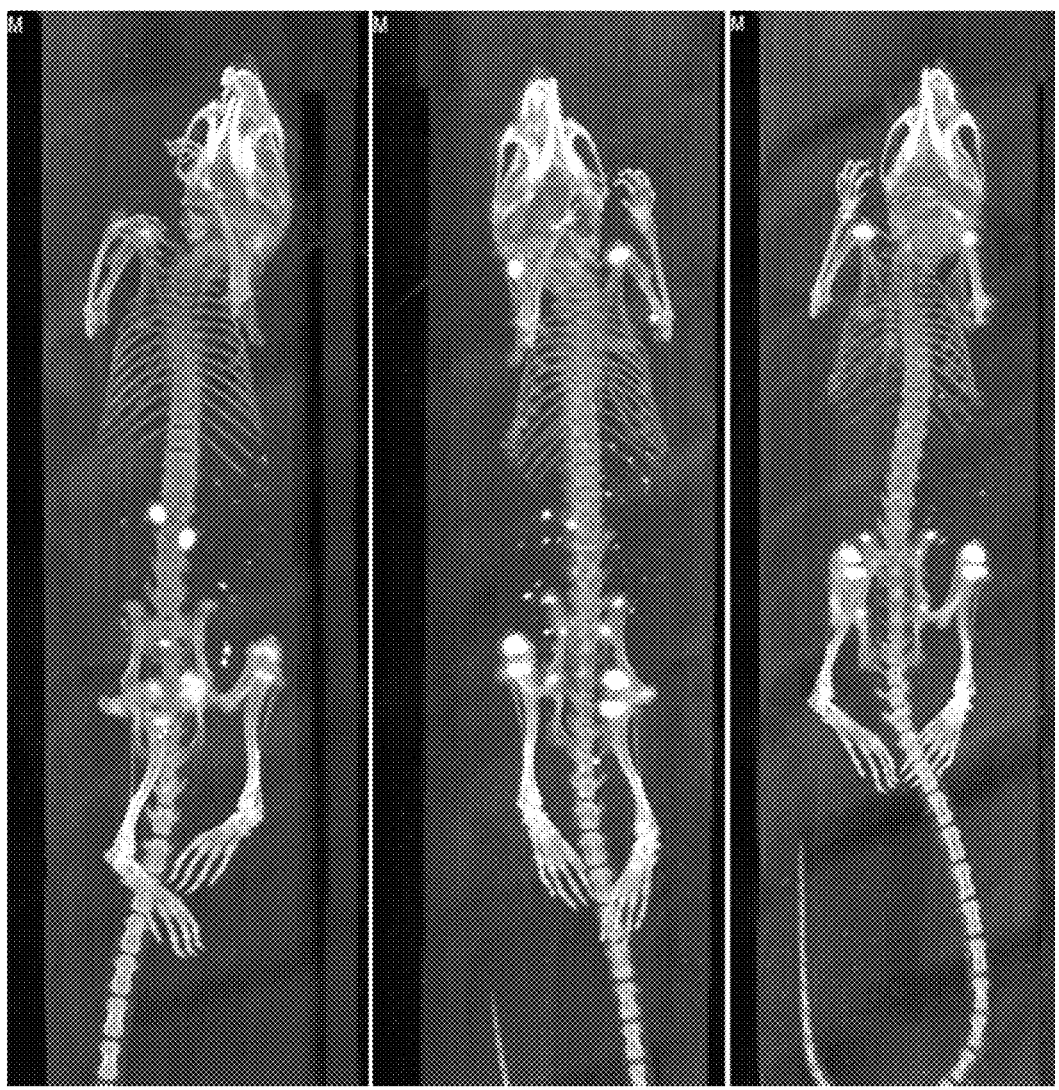
FIG. 5 illustrates SPECT images of mice.

Radio-ITLC results of the saline solution of methylene diphosphonate conjugated $^{99m}TcO_4$— and showed 100% labeling. In these experiments, activities of 2.0×10$^7$Bq of $^{99m}Tc$ were injected into each mouse. Scan times of 45 minutes were employed in imaging while each mouse was anesthetized with isoflurane. FIG. 5 illustrates SPECT images of mice imaged at (a) 1.5 hours (b) 3 hours and (c) 4 hours post injection.

In vivo imaging of normal mice at various time points showed uptake of the $^{99m}Tc$ in the bones as expected (FIG. 5). At the earliest time point, activity was seen in the excretory organs as shown in FIG. 5A, namely the kidneys and bladder. As time progressed, there was clearance of radioactivity from these organs and increased accumulation in the bones and joints as shown in FIGS. 5B and 5C. These data indicate that $^{99m}$Tc produced by the disclosed methods can be used in medical imaging applications.

Example 7

This example illustrates compositions, articles and methods for preparing increased yields of $^{99m}$Tc.

Figure 6:
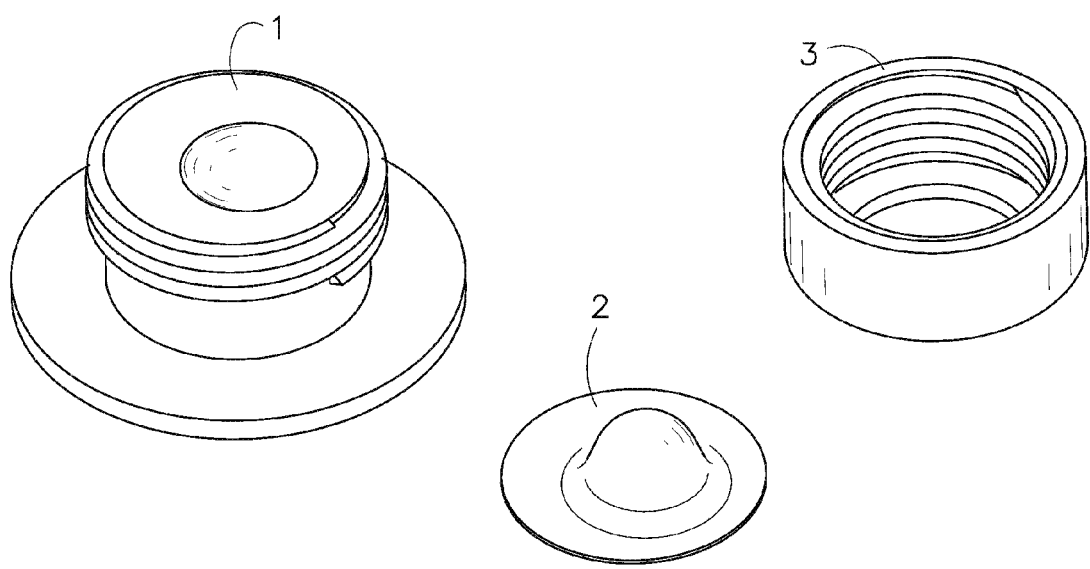
FIG. 6 illustrates components of a target holder apparatus.

In these experiments, a novel target holder was employed, in order to secure $^{100}$Mo$_2$C powder for bombardment. After the powder was pressed in the dimple in a platinum base, it was covered with aluminum foil that was held in place by a screw top lid. FIG. 6 illustrates the components of the target set-up, including platinum base 1, aluminum foil 2 and screw top lid 3. The entire assembly was loaded into the cyclotron.

The platinum base 1 has the following dimensions: diameter of base=0.750 inches; height of riveted area=0.279 inches; diameter across of riveted area=0.4375 inches; diameter of dimple=0.260 inches; depth of dimple 0.044 inches; thread pitch=32 threads per inch.

The aluminum cap has the following dimensions: total diameter=0.500 inches; height=0.250 inches; diameter of opening=0.319 inches.

Pressing of the $^{100}$Mo$_2$C gave a compact powder. However, sintering methods were developed so as to have a more compact structure. Sintering was carried out by heating the pressed powder under vacuum at 600° C. The vacuum conditions employed reduced heat that otherwise may have been lost by thermal currents to surrounding gas molecules.

Bombardment experiments were conducted to demonstrate production levels of $^{99m}$Tc using a sintered target. In these experiments, the current of the proton beam used for bombardment was gradually increased from 5 µA to 20 µA, the maximum bombardment current at which the CS-15 cyclotron operates. The bombardment time was increased to two hours. As shown in Table 3, upon bombardment, sintered targets produced much higher $^{99m}$Tc levels (>20% increase) compared to non-sintered targets.

TABLE 3

| Bombardment parameters: 20 µA, 40 µAhr | |
|---|---|
| Un-sintered powder | Sintered powder |
| 46 mCi | 56 mCi |

All publications, including patent applications, patents, and other references mentioned herein are incorporated by reference, each in its entirety. Any discussion of references cited herein is intended, merely to summarize the assertions made by their authors and no admission is made that any reference or portion thereof constitutes relevant prior art. Applicant reserves the right to challenge the accuracy and pertinency of the cited references.

What is claimed is:

1. A method of synthesizing pertechnetate ($^{99}$TcO$_4^-$), the method comprising: synthesizing $^{100}$MO$_2$C by thermally carburizing $^{100}$MoO$_3$; and bombarding the $^{100}$Mo$_2$C with protons in a cyclotron to yield $^{99}$TcO$_4^-$.

2. A method of synthesizing pertechnetate ($^{99m}$TcO$_4^-$) in accordance with claim 1, further comprising purifying the $^{99m}$TcO$_4^-$ by thermo-chromatography.

3. A method of synthesizing pertechnetate ($^{99}$TcO$_4^-$) in accordance with claim 1, wherein the thermally carburizing comprises:
   (i) converting $^{100}$MoO$_3$ to ammonium heptamolybdate tetrahydrate ((NH$_4$)$_6$Mo$_7$O$_{24}$.4H$_2$O) with 28% NH$_3$ (aq), (ii) converting (NH$_4$)$_6$Mo$_7$O$_{24}$.4H$_2$O to a hexamethyltetramine (HMT)-molybdate complex ((NH$_4$)$_4$(HMT)$_2$Mo$_7$O$_{24}$.4H$_2$O) by reacting the (NH$_4$)$_6$Mo$_7$O$_{24}$.4H$_2$O with NH$_3$(aq) and HMT and (iii) heating the dried HMT-molybdate complex in argon atmosphere to yield $^{100}$Mo$_2$C.

4. A method of synthesizing $^{99m}$Tc pertechnetate in accordance with claim 1, wherein the bombarding the $^{100}$Mo$_2$C comprises bombarding the $^{100}$Mo$_2$C at a current of from about 1 µA, 1 µA up to 20 µA, or about 20 µA.

5. A method of synthesizing $^{99m}$Tc pertechnetate in accordance with claim 1, wherein the bombarding the $^{100}$Mo$_2$C comprises bombarding the $^{100}$Mo$_2$C for about 45 minutes, from 45 minutes to 2 hours, or for about 2 hours.

6. A method of synthesizing $^{99m}$Tc pertechnetate in accordance with claim 1, wherein the bombarding the $^{100}$Mo$_2$C comprises bombarding the $^{100}$Mo$_2$C at a current of about 20 µA for about 2 hours.

7. A method of synthesizing $^{99m}$Tc pertechnetate in accordance with claim 1, further comprising collecting the $^{99m}$Tc$_4^-$ in NaOH.

8. A method of synthesizing $^{99m}$Tc pertechnetate in accordance with claim 2, wherein the thermo-chromatography comprises:
   (i) conditioning the column with acidified water, (ii) passing NaOH containing $^{99m}$TcO$_4^-$ through an ion-exchange column and (iii) eluting the column with a saline solution.

9. A method of synthesizing $^{99m}$Tc pertechnetate in accordance with claim 8, wherein the acidified water has a pH of about 2.

10. A method of synthesizing $^{99m}$Tc pertechnetate in accordance with claim 1, further comprising recycling the $^{100}$Mo$_2$C to form $^{100}$MoO$_3$.

11. A method of synthesizing $^{99m}$Tc pertechnetate in accordance with claim 10, wherein the recycling comprises:
   (i) washing the $^{100}$Mo$_2$C with 28% NH$_3$(aq); and
   (ii) applying the solution from (i) to synthesis of (NH$_4$)$_6$Mo$_7$O$_{24}$.4H$_2$O.

12. A method of synthesizing pertechnetate ($^{99m}$TcO$_4^-$) in accordance with claim 1, further comprising:
   prior to the bombarding, pressing the $^{100}$Mo$_2$C to form a compact powder; and
   sintering the compact powder.

13. A method of synthesizing pertechnetate ($^{99m}$TcO$_4^-$) in accordance with claim 12, wherein the sintering the compact powder comprises heating the compact powder under vacuum at about 600° C.

* * * * *